United States Patent
Wu et al.

(10) Patent No.: US 8,652,549 B2
(45) Date of Patent: Feb. 18, 2014

(54) METHOD FOR POST-EXTRACTING LOW ACYL GELLAN GUM WITH HIGH SOLUBILITY

(75) Inventors: Rongming Wu, Zhejiang (CN); Yanfei Zhong, Zhejiang (CN); Qi Guo, Zhejiang (CN); Yueqiang Shen, Zhejiang (CN); Liping Shen, Zhejiang (CN)

(73) Assignee: Zhejiang DSM Zhongken Biotechnology Co., Ltd., Zhejiang (CN)

( * ) Notice: Subject to any disclaimer, the term of this patent is extended or adjusted under 35 U.S.C. 154(b) by 226 days.

(21) Appl. No.: 13/142,407

(22) PCT Filed: Jun. 2, 2010

(86) PCT No.: PCT/CN2010/000783
§ 371 (c)(1),
(2), (4) Date: Jun. 27, 2011

(87) PCT Pub. No.: WO2011/003270
PCT Pub. Date: Jan. 13, 2011

(65) Prior Publication Data
US 2011/0268843 A1   Nov. 3, 2011

(30) Foreign Application Priority Data
Jul. 9, 2009   (CN) .......................... 2009 1 0158367

(51) Int. Cl.
*C12P 19/04* (2006.01)
*A23L 1/054* (2006.01)
*C08B 37/00* (2006.01)

(52) U.S. Cl.
USPC ............... 426/48; 435/101; 435/41; 435/170; 536/114

(58) Field of Classification Search
None
See application file for complete search history.

(56) References Cited

U.S. PATENT DOCUMENTS

| 4,503,084 A * | 3/1985 | Baird et al. .................... 426/573 |
| 6,605,461 B2 | 8/2003 | Yamazaki et al. |
| 2008/0145505 A1 * | 6/2008 | Bezanson et al. ............. 426/576 |

FOREIGN PATENT DOCUMENTS

| CN | 1932026 A | 3/2007 |
| CN | 101062957 A | 10/2007 |
| CN | 101191138 A | 6/2008 |
| CN | 101597341 A | 12/2009 |

OTHER PUBLICATIONS

Yin et al. (CN 101191138) EPO machine translation claims and description.*
Zhang et al. (CN 101062957) EPO machine translation claims and description.*
Yin et al. (publication No. CN 101191138) EPO machine translation claims and description, published Oct. 27, 2010.*
Zhang et al. (publication No. CN 101062957) EPO machine translation claims and description, published Oct. 31, 2008.*
Shelef et al. ("Microalgae harvesting and processing: a literature review" Report, Solar Energy Research Institute, Golden Colorado, SERI/STR-231-2396, 1984).*

* cited by examiner

*Primary Examiner* — Ruth Davis
*Assistant Examiner* — Emily Cordas
(74) *Attorney, Agent, or Firm* — Drinker, Biddle & Reath, LLP

(57) ABSTRACT

The invention relates to a post-extraction process for preparing low acyl gellan gum having high solubility property, the process comprising the following steps: (1) enzyme treatment of fermentation broth; (2) flocculation of fermentation broth; (3) deacylation treatment; (4) clarification treatment of deacylated solution; (5) dehydration treatment of clarified and deacylated gellan gum solution; (6) ion exchange and decoloration treatment; and (7) drying and milling. The process according to the invention produces a product, which has largely improved solubility, largely improved quality, good appearance, high transparence, and high gel strength.

52 Claims, No Drawings

METHOD FOR POST-EXTRACTING LOW ACYL GELLAN GUM WITH HIGH SOLUBILITY

FIELD OF INVENTION

The invention relates to the field of extraction of substances produced from the fermentation of microorganisms, in particular, to a post extraction process for preparing low acyl gellan gum having the property of high solubility.

BACKGROUND

Gellan gum is an anionic, linear polysaccharide from microorganisms having a molecular weight of up to $2\sim3\times10^5$ daltons. The bacterium for producing gellan gum was originally called as *Pseudomonas elodea*, and later identified as a gram-negative and aerobic *bacillus*, i.e., *Sphingomonas paucimobilis*, based on the characteristics of r-RNA and the fact that the bacterium contains the glycolipid sphingosine. It can be said that gellan gum is one of the best thickening agents and one of the best stabilizers at present, based on the excellent properties, and also has a good gelation nature. The gel from gellan gum is easy to use, and has a good flavor-releasing characteristic, and has a high stabilization to heat. In addition, the gel is easy to melt in mouths, and has a high transparence. The time and temperature for gelation are controllable, and the gelation is not easy to be influenced by the variations of pH. The product is stable and has various texture properties, and so on. Gellan gum has two types, in term of forms. One is low acyl gellan gum, i.e., the acyl groups on the main chain of gellan gum molecule are removed by a heat and base treatment, either completely or partially. The other is native gellan gum, i.e., high acyl gellan gum. The high acyl type gellan gum can form soft, elastic, but not brittle gels while the low acyl type gellan gum can form firm, non-elastic, but very brittle gels. Gellan gum can work as a gelling agent with the proviso that it must be dissolved completely in water to form an aqueous solution of colloid.

Many hydrophilic colloids do not show good colloid properties in some circumstances due to incomplete dissolution. In an actual production, a lot of users can not use gellan gum properly for not knowing the dissolution property well. So, among the factors that influence the gelation property of gellan gum, it needs to firstly pay attention to the dissolution of colloid.

The dissolution process of gellan gum comprises two steps. Firstly, the gellan gum is evenly dispersed in cold water, and then heat is given to the mixture so that gellan gum can hydrate with water molecules to form gellan gum solution, thereby reaching the status of complete dissolution.

In the food industry, the even dispersion of hydrophilic colloid is very important. In a production, it needs a large amount of agitation treatment sometime so that the formation of "fish eyes" can be avoided due to incomplete hydration caused by colloid aggregations, agglomeration, or swelling effects. In the operation of food industry at present, in order to make low acyl gellan gum have a good dispersivity, the gellan gum may be firstly mixed with a chelating agent, white sugar or other powders as adjuvant, vegetable oils, propylene alcohol, and the resultant mixture is then plunged into cold water, if the formulation and the processing condition for production allow. This treatment can seclude the fine and small grains of gellan gum and reach the effect of the even dispersion in water. However, some specific foods do not use other aiding materials, and this will significantly influence the property of dispersivity of low acyl gellan gum.

The temperature of hydration for low acyl gellan gum with water is very sensitive to the ions existing in the environment, especially to divalent cations. If the low acyl gellan gum has been admixed with salts, it can only be partially hydrated with cold deionized water. The further hydration of this colloid will be blocked by divalent cations, in other water quality environment, for example, in solid water. Hereby, for the colloid, it is a must of adding a chelating agent, or heating, or both of the two methods as mentioned, to reach a full hydration.

Therefore, we can see that it needs to ensure a complete dispersion and a complete hydration of low acyl gellan gum during the dissolution process. If both of the two conditions as mentioned above can not be satisfied or only one of them can be satisfied, the following circumstances will appear, including a largely reduced gel property, a bad gel texture not reaching the ideal requirement, and so on. But, for the food-level low acyl gellan gum produced in industrial and large-scale production at present, the dissolution property has a large defect. The main deficiencies are embodied in: 1. The product has a very bad dispersivity. It can easily form aggregations during the alone dissolution process in cold water. There is a must of high speed agitation or incorporation of other adjuvant powders by a dry mixing so that the dispersivity property can be improved. If the formulation does not contain other powdery components or the operation does not allow the introduction of a high speed agitation, the low dispersivity of the product will heavily influence the ensuing treatments. 2. The product has a poor hydration property. To ensure a full hydration with water, the 0.5% solution of low acyl gellan gum product in water needs to be heated to a temperature above 80° C., and maintained at the temperature for 5 minutes. If a food formulation contains a thermo-instable adjuvant, this operation will heavily influence the property of this adjuvant. In addition, for some specific food stuff, it needs to keep the temperature during the processing conditions in production at the normal temperature. That is to say, the processing temperature needs to be kept at a temperature below 35° C. For a food product of this type, the low acyl gellan gum having the general properties will have no use. So, it will be a large promotion in applications of gellan gum in food industry if a low acyl gellan gum having high solubility is produced and provided.

SUMMARY OF INVENTION

One aim of the invention lies in that it provides a process for extracting low acyl gellan gum having a high solubility property, i.e., low acyl gellan gum having high dispersivity and high hydration properties.

The process for extracting low acyl gellan gum having a high solubility property according to the invention comprises an enzyme treatment for gellan gum-containing fermentation broth, a flocculation treatment of acid/chelating agent/lower alcohol mixture system, a deacylation treatment, a clarification treatment of the deacylated gellan gum solution, an ion exchange treatment, a hydration treatment of the deacylated gellan gum solution, drying and granulation. In particular, the process comprises the following steps:

Enzyme Treatment of Fermentation Broth;

Into a fermentation broth, different enzyme preparations are added sequentially, and the temperatures are maintained to conduct the zymolysises so that the insoluble impurities and bacterial debris can be removed from the fermentation broth as much as possible. In details, after an enzyme preparation is added and the temperature has been kept for the zymolysis, another enzyme is added and the temperature is kept to conduct another zymolysis, and following zymolysises if necessary go on like that.

(2) Flocculation of Fermentation Broth;

Into the fermentation broth treated by enzyme in Step (1), the mixture system of acid/chelating agent/lower alcohol is added to flocculate, and then a solid-liquid separation is conducted to remove a large part of water and pigments from the fermentation broth. A raw product, the concentrated gellan gum, is obtained;

(3) Deacylation Treatment

The floccule product obtained in Step (2) is re-dissolved and the resultant solution is subjected to a high temperature and base treatment to deacylate;

(4) Clarification Treatment of Deacylated Solution

The deacylated solution obtained in Step (3) can be filtered by a filtration treatment, so that a clarified low acyl gellan gum solution is obtained;

(5) Dehydration Treatment of Clarified Deacylated Gellan Gum Solution

Into the gellan gum-deacylated clarified solution obtained in Step (4), an alkali salt is added to form a gel, and the gel is pressed to dehydrate;

(6) Ion Exchange and Decoloration Treatment

The gellan gum obtained in Step (5) is cut into fine and small grains, most of the divalent cations existing in the gellan gum is removed by ion exchange; and then, the treated solution is pressed to dehydrate, and the dehydrated gellan gum is immersed with a lower alcohol along with agitation, and a filtration is conducted to completely remove the colorous substances;

(7) Drying and Milling;

The solid materials, i.e., gellan gum obtained in Step (6), is dried and milled. By granulation, a highly-transparent low acyl gellan gum product is obtained.

More particularly, the post-extraction process according to the invention comprises:

Enzyme treatment of fermentation broth;

Into the fermentation broth, sequential additions of cellulase, lysozyme and proteinase are done, at different concentrations, which have been dissolved and dispersed with a little amount of water. Then, the temperatures are kept for different time periods for the performance of zymolysises. The proteinase may be a neutral proteinase or an acidic proteinase.

2. Flocculation of Fermentation Broth

The temperature of the fermentation broth treated in Step (1) by enzymes is reduced to a temperature below 30° C., and the mixture system of acid/chelating agent/lower alcohol is added to form the fiber-like flocculent. The fiber-like flocculent is pressed to a solid-liquid separation. In this treatment, the acid, the chelating agent and the lower alcohol in the system of acid/chelating agent/lower alcohol may be firstly mixed and then added into the fermentation broth together, or they may be added into the fermentation broth in a sequential order.

3. Deacylation Treatment (3.1) The product obtained via the flocculation in Step (2) is broken up and dissolved with deionized water in the amount having the weight of 10~20 times of the weight of the product. The temperature is raised up to 80~90° C. and an intensive agitation is conducted so that a complete dissolution reaches;

(3.2) Into the gellan gum solution obtained in Step (3.1), a base is added to adjust the pH value into the range of 9.5~11. The temperature is kept at a temperature in the range of 85~90° C. for a time of 10~15 minutes so that the glycerol groups and the acetyl groups on the main chain of gellan gum molecules are removed;

(3.3) Into the deacylated gellan gum solution obtained in Step (3.2), an acid is added to adjust the pH value to the neutral condition.

4. Clarification Treatment of Deacylated Solution

With a plate-and-frame or chamber-type filter press, a high speed centrifuge, or a microporous membrane filter, the deacylated gellan gum solution obtained in Step (3.3) is subjected to a clarification treatment. The temperature for the clarification treatment is preferably a temperature above 60° C. to prevent from the formation of gel from the solution. The transmittancy of the clear solution so obtained is above 92%.

5. Dehydration Treatment of Deacylated Gellan Gum Solution

Into the deacylated, clarified gellan gum solution obtained in Step (4), a proper amount of a salt of alkali metal cations is added. The formed gel is dehydrated by a press and the curds or sheets of low acyl gellan gum having about 80% of water are obtained.

6. Ion Exchange and Decoloration Treatment

The low acyl gellan gum having about 80% of water obtained in Step (5) is cut into grains, and the grains are plunged into water in the amount of 3~5 times of the weight of the grains. The water has been pretreated by a suitable monovalent metal salt. Let the water immerse the grains of low acyl gellan gum for a while, and with a high speed agitation. By ion exchange, the colloid in divalent cations salts format is converted into monovalent cations salts format. The treated gellan gum solution is pressed to dehydrate, and then, the solid material is added into a lower alcohol solution in the amount of 2 times of the weight of the solid material. Let the lower alcohol immerse the solid material for a while, and with a high speed agitation. After this, a filtration is conducted to reach the result of complete removal of pigments.

7. Drying and Milling

The product prepared in Step (6) is dried at the temperature of 75~80° C. and milled. After this, it is granulated. 95% of the particles pass a sieve of 40 meshes.

Most particularly, the processing conditions for each step of the invention are:

In Step 1, the enzymes as added, and the conditions as used are described as follows, respectively. For cellulase, the concentration is preferably 500~2000 ppm, more preferably 1000~1500 ppm; the temperature for zymolysis is preferably 40~50° C., more preferably 43~45° C.; and the time for zymolysis is preferably 4 to 8 hours, more preferably 5 to 6 hours. For lysozyme, the concentration is preferably 50~300 ppm, more preferably 100~200 ppm; the temperature for zymolysis is preferably 30~40° C., more preferably 35~37° C.; the time for zymolysis is preferably 2 to 4 hours, more preferably 2.5 to 3.5 hours. For proteinase, the concentration is preferably 100~1000 ppm, more preferably 300~500 ppm; the temperature for zymolysis is preferably 30~40° C., more preferably 30~35° C.; the time for zymolysis is preferably 1 to 5 hours, more preferably 2 to 3 hours. The proteinase may be a neutral proteinase or an alkaline proteinase, and the concentration is calculated with the fermentation broth as the basis.

In Step 2, among the acid/chelating agent/lower alcohol mixture system as used, the acid may be selected from the group consisting of an inorganic acid or an organic acid. The inorganic acid may be selected from, but not limited to, one or more of hydrochloric acid, sulfuric acid or phosphoric acid. The organic acid may be selected from, but not limited to, one or more of formic acid, acetic acid, citric acid, malic acid or tartaric acid. In practical production, the acid as used is preferably an inorganic acid, more preferably hydrochloric acid.

The amount of acid as used is the amount that makes the fermentation broth liquid system's pH adjusted to 2.5~3.5.

In Step 2, the acid used is preferably firstly formulated into a solution having the concentration of 10%.

In Step 2, among the used acid/chelating agent/lower alcohol mixture system, the chelating agent may be selected from, but not limited to, one or more of sodium citrate, tripotassium citrate, sodium hexametaphosphate, potassium hexametaphosphate, sodium pyrophosphate and potassium tripolyphosphate. For the preferable use, the chelating agent is selected from the group consisting of sodium citrate and sodium hexametaphosphate, more preferably sodium citrate. The amount of the chelating agent added is preferably, calculated in the fermentation broth, the concentration of 200~1000 ppm, more preferably 500~700 ppm.

In Step 2, among the used acid/chelating agent/lower alcohol mixture system, the lower alcohol may be selected from the group consisting of one or more of ethanol, isopropanol, and n-butanol. Preferably, it is selected from ethanol and isopropanol, more preferably, it is isopropanol. The amount of the lower alcohol is used at the amount of preferably 2~4 times of the volume of the fermentation broth liquid, more preferably 2.5~3.5 times of the volume of the fermentation broth liquid.

In Step 2, the device for the solid-liquid separation may be selected from, but not limited to a chamber-type polypropylene plate-and-frame filter press or a sack press. It is preferable to use a chamber-type polypropylene plate-and-frame filter press.

In Step 3.1, preferably, the broken fibers of gellan gum have the length of not more than 10 cm, and the water content in the fibers is about 80%.

In Step 3.1, the broken fibers of gellan gum are dissolved with deionized water of the amount of 10 to 20 times of the weight of the broken fibers, preferably with deionized water of the amount of 15~20 times of the weight of the broken fibers. Heat the solution as formed so that the temperature reaches 80~95° C., more preferably 85~90° C.

In Step 3.2, for the purpose of adjustment of pH, the base is selected from, but not limited to, one or more of NaOH, KOH, Na2CO3, and K2CO3. It is preferable to select from NaOH and KOH. It is more preferable to use NaOH.

In Step 3.2, by using the base, the pH value is adjusted to the 9.5~11 range. More preferably, the pH value is about 10.

In Step 3.2, the temperature is maintained between 85~90° C. More preferably, the temperature is maintained between 86~88° C.

In Step 3.2, the time lasts for 10~15 minutes. More preferably, the time lasts about 10 minutes.

In Step 3.2, for the purpose of adjustment of pH, the base is preferably firstly formulated into a solution having the concentration of 10%.

In Step 3.3, for the purpose of adjustment of pH, the acid may be an inorganic acid, or the acid may be an organic acid. The inorganic acid includes, but not limited to, one or more of hydrochloric acid, sulfuric acid and phosphoric acid. The organic acid may be selected from, but not limited to, one or more of formic acid, acetic acid, citric acid, malic acid or tartaric acid. In the practice of production, it is preferable to use the acid, i.e., an inorganic acid. More preferably, it is to use hydrochloric acid. The acid is used at the amount that adjusts the pH of the fermentation broth liquid to about 7.

In Step 3.3, for the purpose of adjustment of pH, the acid is preferably firstly formulated into a solution having the concentration of 10%.

In Step 4, the device for clarification may be, but not limited to, a plate-and-frame or chamber-type filter press, a high speed centrifuge, or a microporous membrane filter. It is preferable to use a plate-and-frame filter press, or a chamber-type filter press.

In Step 4, during the clarification treatment, the temperature is preferably at a temperature above 65° C. to prevent from the formation of gel from the solution. More preferably, the temperature is about 75° C.

In Step 5, for the purpose of the formation of gel, the alkali metal salts to be added include, but not limited to, a monovalent alkali metal (for example, one or more selected from potassium chloride, sodium chloride, potassium sulfate, and sodium sulfate), divalent alkali metal (for example, one or more selected from calcium chloride, and magnesium chloride) and a multivalent metal (for example, ferric chloride), and so on. Preferably, the salts of the monovalent and divalent alkali metals are used. If considering the factor of cost, it may be more preferable to use the salts of divalent alkali metals.

In Step 5, for the purpose of the formation of gel, when a salt of a monovalent alkali metal is added, the amount is that accounts for 0.8~1.2% (weight percent) of the weight of the clear gel solution; and when a salt of a divalent metal is added, the amount is that accounts for 0.05~0.1% (weight percent) of the weight of the clear gel solution.

In Step 5, for the purpose of the formation of gel, preferably, the added metal salt is firstly formulated into a solution having the 30% concentration.

In Step 5, during the dehydration by pressing, the device for solid-liquid separation as used may be selected from, but not limited to a chamber-type polypropylene plate-and-frame filter press or a sack press. Preferably, the device is a chamber-type polypropylene plate-and-frame filter press.

In Step 6, with the use of a gel cutter, the low acyl gellan gum is cut into column-shaped grains. The grains have a diameter of less than 3 mm, and a length of less than 12 mm.

In Step 6, as used, the monovalent metal salt includes, but not limited to, a soluble monovalent alkali metal salt (for example, one or more selected from potassium chloride, sodium chloride, potassium sulfate, and sodium sulfate). The amount is, as calculated in the solution, preferably with the concentration reaching 5000~10000 ppm, more preferably 6000~8000 ppm.

In Step 6, as used, the device for dehydration by pressing is a sack press.

In Step 6, the lower alcohol as used may be one or more selected from the group consisting of ethanol, isopropanol, and n-butanol. Preferably, the lower alcohol is selected from ethanol and isopropanol. More preferably, it is isopropanol. The amount is, preferably 2~4 times of the weight of the wet grains of gellan gum, more preferably 2.5~3.5 times of the weight of the wet grains of gellan gum.

In Step 7, the device for drying as used may be selected from, but not limited to, a vacuum dryer or a boiling dryer. The temperature is controlled between 75~80° C. And, the time period is controlled between 1 to 1.5 hours.

In Step 7, the particles formed by granulation need to reach the specification that 95% of them can pass a screen of 40 meshes.

A detailed description of the present invention is illustrated with reference to the following examples, with the aim of providing a better understanding of the invention. But, these examples are non-limited, and provided only for elucidating the invention, not to limit the scope of the invention.

EXAMPLE 1

A. Into to a flocculation tank which has held 10 m3 of gellan gum-containing fermentation broth, 15 kg of cellulase is added along with agitation, and the temperature is kept at 45° C., and a slow agitation is conducted for 5.5 hours. After this, 2 kg of lysozyme is added and the temperature is kept at 35° C., and a slow agitation is conducted for 3 hours. Later, 4 kg of neutral proteinase is further added and the temperature is kept at 33° C., a slow agitation is conducted for 2.5 hours.

B. Into the above-described feed liquid, hydrochloric acid (10% solution)/sodium hexametaphosphate/ethanol solution system is slowly added until the feed liquid has the pH of 2.5, and an agitation is continued for 10 minutes. The feed liquid is pumped into a chamber-type plate-and-frame filter press to filtrate. The filtrate is exited into a wastewater treatment station, and the cake with the weight of 850 kg as obtained is kept for later use.

C. The cake obtained in B is firstly broken up into short fibers by a beater, and then the short fibers are added into deionized water of the amount having the weight of 15 times of the weight of the short fibers. The solution is heated so that the temperature is raised up to 90° C. KOH having the 10% concentration is added to adjust pH to 10.0. And on the condition that the temperature is kept at 90° C., a slow agitation is conducted for 10 minutes. Then, hydrochloric acid having the concentration of 10% is added to adjust back pH to 7.0, and the solution so obtained is subjected to the next step.

D. Into the solution obtained in C, a proper amount of diatomite is added and is dispersed evenly by agitation, and the temperature is controlled at 75° C. With a chamber-type polypropylene plate-and-frame filter press, which has been pre-coated with the filtration aid, i.e., diatomite, the gellan gum solution is cyclically filtrated until the so-clarified gellan gum solution has a transmittancy of larger than 92% measured by a spectrometer. The clarified solution is entered into a gel tank.

E. The temperature of the clarified gellan gum solution obtained in D should be maintained above 65° C., which can prevent from the formation of gel. Then, into the solution, 400 L of potassium chloride having the concentration of 30% is added, and a slow agitation is conducted for 5 minutes. After this, a forced cooling is performed so that the temperature is reduced to below 50° C. The colloid, which was formed as rigid and brittle form, is pressed with a chamber-type polypropylene plate-and-frame filter press. 450 kg of curds or sheets of gellan gum having a water content of about 80% is obtained.

F. The curds or sheets of gellan gum obtained in E are cut into column-shaped grains by a gel cutter. The grains have a diameter of less than 3 mm and a length of less than 12 mm. The grains so-obtained of gellan gum are plunged into deionized water in the mass of 3 times of the mass of the grains, and at the same time, the solution of potassium chloride is added until the concentration thereof reaches 5000 ppm. A slow agitation is imparted to the solution for 10 minutes. After this, the solution is filtrated with a filter cloth. The filter residue is immersed with ethanol solution in the amount of 2.5 times of the weight of the filter residue, and a high-speed agitation is conducted for 30 minutes. The ethanol solution is removed with a sack press. Thereby, 450 kg of loose grains of gellan gum is obtained.

G. The product obtained in F is dried with a boiling dryer. The drying is carried out at the temperature of 75° C. Then, the dried product is milled. After milling, the product is subjected to a granulation process so that 95% of particles can pass a sieve of 40 meshes. The product, i.e., low acyl gellan gum, in the amount of 90 kg, is obtained.

EXAMPLE 2

A. Into a tank for flocculation, which has held 10 m3 of gellan gum-containing fermentation broth, 10 kg of cellulase is added along with agitation and the temperature is kept at 43° C. A slow agitation is conducted for 5 hours. After this, 1 kg of lysozyme is further added and the temperature is kept at 37° C. A slow agitation is conducted for 2.5 hours. After this, 4 kg of alkaline proteinase is further added and the temperature is kept at 35° C. A slow agitation is conducted for 3.0 hours.

B. Into the above-described feed liquid, acetic acid (10% solution)/sodium citrate/isopropanol solution system is added until the feed liquid reaches pH 2.5. An agitation is continued for 10 minutes. The feed is then pumped into a chamber-type plate-and-frame filter press with a pump to filtrate. The filtrate is entered into a wastewater treatment station. 850 kg of a cake is obtained for later use.

C. The cake obtained in B is firstly broken up into short fibers with a beater. Then, the short fibers are added into deionized water in the amount of 15 times of the short fibers in weight. The solution is heated so that the temperature is raised up to 90° C. NaOH having the 10% concentration is added to adjust pH to 10.0. On the condition that the temperature is kept at 90° C., a slow agitation is conducted for 10 minutes. Then, acetic acid having the 10% concentration is added to adjust back pH to 7.0. The solution so-obtained is subjected to the next step.

D. The solution obtained in C is subjected to a clarification operation by using high speed centrifugation until the so-obtained clarified gellan gum solution has a transmittancy of 92% determined by a spectrometer. The clarified solution is entered into a gel tank.

E. The temperature of the clarified gellan gum solution obtained in D should be maintained at a temperature of above 65° C. to prevent from the formation of gel. Into the solution, 400 L of sodium chloride solution having the 30% concentration is added and a slow agitation is conducted for 5 minutes. After this, a forced cooling is performed so that the temperature is reduced to a temperature below 50° C. The colloid, as formed in the rigid and brittle format, is pressed with a sack press. 500 kg of sheets or curds of gellan gum having a water content of about 80% is obtained.

F. he curds or sheets of gellan gum obtained in E are cut into column-shaped grains by a gel cutter, with the grains having a diameter of less than 3 mm, and a length of less than 12 mm. The grains of gellan gum are plunged into deionized water in the amount of 3 times in mass of the grains of gellan gum, and at the same time, sodium chloride is added into the solution so that the concentration of sodium chloride reaches 7000 ppm. A slow agitation is conducted to the solution for 10 minutes. After the agitation, the solution is filtered with filter cloth. The filtrate is immersed with isopropanol solution in the amount of 2.5 times of the weight of the filtrate and a quick agitation is conducted for 30 minutes. With a sack press, the isopropanol solution is removed and 450 kg of loose grains of wet gellan gum is obtained.

G. he product obtained in F is passed into a boiling dryer to be dried at the temperature of 75° C. The dried product is milled and granulated into granules so that 95% of granules pass a sieve of 40 meshes. 90 kg of the product of low acyl gellan gum is obtained.

EXAMPLE 3

A. Into a tank for flocculation, which contains 10 m3 of gellan gum-containing fermentation broth, 10 kg of cellulase is added under agitation, and then the temperature is kept at 43° C. and a slow agitation is conducted for 5 hours. After this, 1 kg of lysozyme is further added and the temperature is kept at 37° C., and a slow agitation is conducted for 2.5 hours.

Then, 4 kg of alkaline proteinase is further added and the temperature is kept at 35° C. and a slow agitation is conducted for 3.0 hours.

B. Into the above-described feed liquid, phosphoric acid (10% solution)/sodium pyrophosphate/ethanol solution system is slowly added until the pH of the feed liquid reaches 3.0. An agitation is conducted for 10 minutes. The feed liquid is pumped into a chamber-type plate-and-frame filter press to perform a filtration. The filtrate is exited into a wastewater treatment station, and 850 kg of cake is obtained for later use.

C. The cake obtained in B is firstly broken up into short fibers with a beater. Deionized water in the amount of 15 times of the weight of the fibers as obtained above is added to form a solution, and the solution is heated until the temperature reaches 90° C. Into the solution, NaOH having the concentration of 10% is added to adjust pH to 10.0. Under the condition that the temperature is kept at 90° C., a slow agitation is conducted for 10 minutes. Then, phosphoric acid having the concentration of 10% is added to adjust back pH to 7.0, and the so-obtained solution is subjected to the next step.

D. The solution obtained in C is filtered with a microporous filter membrane until the so-obtained clarified gellan gum solution has a transmittancy of above 92% measured by a spectrometer. The clarified solution is entered into a gel tank.

E. As to the clarified gellan gum solution obtained in D, the temperature needs to be kept at a temperature of above 65° C. so that the gel formation is prevented. Into the solution, 400 L of sodium chloride solution having the concentration of 30% is added and a slow agitation is conducted for 5 minutes. Then, the temperature is forcedly decreased into a temperature below 50° C. The colloid of the formed firm and brittle gel is pressed with a chamber-type polypropene plate-and-frame filter press, and 500 kg of sheets or curds of gellan gum having the water content of about 80% is obtained.

F. The curds or sheets of gellan gum obtained in E are cut into column-shaped grains by a gel cutter, with the grains having a diameter of less than 3 mm, and a length of less than 12 mm. The grains of gellan gum are plunged into deionized water in the amount of 3 times of the mass of the grains of gellan gum, and at the same time, potassium sulfate is added until the concentration thereof reaches 8000 ppm, and a slow agitation is conducted to the solution for 10 minutes. After this, the solution is filtered with filter cloth. The filtrate is immersed with ethanol solution in the amount of 2.5 times of the weight of the filtrate, and a quick agitation is conducted for 30 minutes and the ethanol solution is removed with a sack press. 450 kg of loose grains of wet gellan gum is obtained.

G. The product obtained in F is passed into a vacuum dryer and dried at the temperature of 75° C. The dried product is milled and granulated into granules so that 95% of the granules can pass a sieve of 40 meshes. 90 kg of low acyl gellan gum product is obtained.

Compared with the existing post-extraction methods of preparing low acyl gellan gum, the process according to the invention has the following advantages:

1. The solubility of the product has a large improvement. At the temperature of about 30° C., a good dispersion and dissolution can realize for this product. But, for the general gellan gum products, it is easy to incur associations and a complete dissolution can only occur with the proviso that the temperature must be kept above 80° C.

2. The quality of product is improved largely, reaching the oversea advance level. The appearance of product is good, the transmittancy of product is high, and the gel strength of the product is high. In particular, the chromaticity of the product is above 83%, and the transmittancy of the product is above 87%, and the gel strength is above 1000 g/cm2.

3. Most of the divalent metal cations are removed by the chelating operation during the later phrase, which makes the slightly whitening phenomenon of the formed gel disappeared and improves the quality of the product.

What we claimed is:

1. A post extraction process for preparing low acyl gellan gum having high solubility property, the process comprises the following steps:
   (1) Enzyme treatment of fermentation broth:
   Into the fermentation broth, different enzymes preparations are added and the temperatures are kept to conduct the zymolysises;
   (2) Flocculation of fermentation broth:
   Into the fermentation broth treated by enzymes in Step (1), an acid/chelating agent/lower alcohol mixture system is added to flocculate, and then a solid-liquid separation is conducted;
   (3) Deacylation treatment:
   The flocculate obtained in Step (2) is re-dissolved, and subjected to deacylation treatment via high temperature and base;
   (4) Clarification treatment of deacylated solution:
   The deacylated solution obtained in Step (3) is subjected to a filtration treatment, and a clarified low acyl gellan gum solution is obtained;
   (5) Dehydration treatment of clarified deacylated gellan gum solution:
   Into the clarified deacylated gellan gum solution obtained in Step (4), an alkali salt is added to form a gel, and the gel is pressed to dehydrate;
   (6) Ion exchange and decoloration treatment:
   The gellan gum obtained in Step (5) are cut into grains, and most of the divalent cations in the gellan gum are removed via ion exchange, and the treated solution is pressed to dehydrate and the dehydrated gellan gum is immersed with lower alcohol under agitation, and subjected to a filtration;
   (7) Drying and milling:
   The solid material of gellan gum obtained in Step (6) is dried and milled and granulated.

2. The process according to claim 1, wherein in Step (1), a cellulase, a lysozyme and a proteinase are added respectively.

3. The process according to claim 2, wherein, for the cellulase, the concentration is 500~2000 ppm, the temperature for zymolysis is 40~50° C., and the time for zymolysis is 4 to 8 hours; and for the lysozyme, the concentration is 50~300 ppm, the temperature for zymolysis is 30~40° C., the time for zymolysis is 2 to 4 hours; and for the proteinase, the concentration is 100~1000 ppm, the temperature for zymolysis is 30~40° C., the time for zymolysis is 1 to 5 hours.

4. The process according to claim 3, wherein, for the cellulase, the concentration is 1000~1500 ppm, the temperature for zymolysis is 43~45° C., the time for zymolysis is 5 to 6 hours; and for the lysozyme, the concentration is 100~200 ppm, the temperature for zymolysis is 35~37° C., the time for zymolysis is 2.5 to 3.5 hours; and for the proteinase, the concentration is 300~500 ppm, the temperature for zymolysis is 30~35° C., and the time for zymolysis is 2 to 3 hours.

5. The process according to claim 3, wherein the proteinase is a neutral proteinase or an alkaline proteinase.

6. The process according to claim 1, wherein in Step (2), the acid among the acid/chelating agent/lower alcohol mixture system as used is an inorganic acid or an organic acid.

7. The process according to claim 6, wherein the acid is an inorganic acid.

8. The process according to claim 7, wherein the inorganic acid is one or more selected from hydrochloric acid, sulfuric acid, and phosphoric acid.

9. The process according to claim 8, wherein the acid is hydrochloric acid.

10. The process according to claim 6, wherein the organic acid is one or more selected from formic acid, acetic acid, citric acid, malic acid and tartaric acid.

11. The process according to claim 6, wherein, among the acid/chelating agent/lower alcohol mixture system as used, the chelating agent is one or more selected from sodium citrate, tripotassium citrate, sodium hexametaphosphate, potassium hexametaphosphate, sodium pyrophosphate, and potassium tripolyphosphate.

12. The process according to claim 11, wherein the chelating agent is selected from sodium citrate and sodium hexametaphosphate.

13. The process according to claim 12, wherein the chelating agent is sodium citrate.

14. The process according to claim 6, wherein, among the acid/chelating agent/lower alcohol mixture system as used, the lower alcohol is one or more selected from ethanol, isopropanol, and n-butanol.

15. The process according to claim 14, wherein the lower alcohol is selected from ethanol and isopropanol.

16. The process according to claim 15, wherein the lower alcohol is isopropanol.

17. The process according to claim 1, wherein in Step (2), a chamber-type polypropylene plate-and-frame filter press or a sack press is used to conduct the solid-liquid separation.

18. The process according to claim 17, wherein a chamber-type polypropene plate-and-frame filter press is used to conduct the solid-liquid separation.

19. The process according to claim 1, wherein, Step (3), i.e., the deacylation treatment, is divided into:
   (3.1) the flocculate obtained in Step (2) is broken up and dissolved with deionized water in the amount of 10~20 times of the weight of the flocculate, and the temperature is raised up to 80~90° C., with a complete agitation, so that a complete dissolution reaches; and
   (3.2) Into the gellan gum solution obtained in Step (3.1), a base is added to adjust the pH value into the range of 9.5~11, and the temperature is kept at 85~90° C. for 10~15 minutes; and
   (3.3) Into the deacylated gellan gum solution obtained in Step (3.2), an acid is added to adjust the pH value into the neutral point.

20. The process according to claim 19, wherein, in Step (3.1), deionized water in the amount of 15~20 times of the weight of the flocculate is used, and the temperature is raised to 85~90° C.; and in Step (3.2), the pH value is adjusted to 10, and the temperature is kept at 86~88° C. for a time period of 10 minutes.

21. The process according to claim 19, wherein, in Step (3.2), the base used for adjustment of pH is one or more of NaOH, KOH, Na2CO3, and K2CO3.

22. The process according to claim 21, wherein the base is NaOH or KOH.

23. The process according to claim 22, wherein the base is NaOH.

24. The process according to claim 19, wherein, in Step (3.3), the acid is an inorganic acid or an organic acid.

25. The process according to claim 24, wherein the acid is an inorganic acid.

26. The process according to claim 25, wherein the inorganic acid is one or more selected from hydrochloric acid, sulfuric acid and phosphoric acid.

27. The process according to claim 26, wherein the acid is hydrochloric acid.

28. The process according to claim 24, wherein the organic acid is one or more selected from formic acid, acetic acid, citric acid, malic acid and tartaric acid.

29. The process according to claim 1, wherein Step (4) uses a plate-and-frame or a chamber-type filter press, a high speed centrifuge, or a microporous filter membrane, to conduct the clarification treatment to the deacylated gellan gum solution obtained in Step (3).

30. The process according to claim 29, wherein a plate-and-frame or a chamber-type filter press is used to conduct the clarification treatment to the deacylated gellan gum solution.

31. The process according to claim 29, wherein, in Step (4), during the clarification treatment, the temperature is above 65° C.

32. The process according to claim 31, wherein, in Step (4), during the clarification treatment, the temperature is at 75° C.

33. The process according to claim 1, wherein, in Step (5), the alkali salt is selected from the group consisting of a monovalent alkali metal, a divalent alkali metal and a polyvalent alkali metal.

34. The process according to claim 33, wherein the alkali salt is selected from a monovalent alkali metal salt and a divalent alkali metal salt.

35. The process according to claim 33, wherein the alkali salt is a divalent alkali metal salt.

36. The process according to claim 33, wherein the monovalent alkali metal is one or more selected from potassium chloride, sodium chloride, potassium sulfate, and sodium sulfate.

37. The process according to claim 35, wherein the divalent alkali metal is selected from calcium chloride, and magnesium chloride.

38. The process according to claim 33, wherein the polyvalent alkali metal is ferric chloride.

39. The process according to claim 1, wherein, in Step (5), a chamber-type polypropylene plate-and-frame filter press or a sack press is used to press to dehydrate.

40. The process according to claim 39, wherein a chamber-type polypropylene plate-and-frame filter press is used to press to dehydrate.

41. The process according to claim 1, wherein, in Step (6), a gel cutter is used to cut the low acyl gellan gum into column-shaped grains, with the grains having a diameter of less than 3 mm, and a length of less than 12 mm.

42. The process according to claim 1, wherein, in Step (6), the ion exchange is conducted by adding a monovalent metal salt, and wherein the monovalent metal salt may be a soluble monovalent alkali metal salt, and the amount is that makes the concentration of the salt in the solution reaches 5000~10000 ppm.

43. The process according to claim 42, wherein the amount of the monovalent metal salt in the solution is that makes the concentration reach 6000~8000 ppm.

44. The process according to claim 42, wherein the soluble monovalent alkali metal salt is one or more selected from potassium chloride, sodium chloride, potassium sulfate, and sodium sulfate.

45. The process according to claim 42, wherein, in Step (6), the device for pressing and dehydrating is a sack press.

46. The process according to claim 41, wherein, in Step (6), the lower alcohol is one or more selected from ethanol, isopropanol, and n-butanol.

47. The process according to claim 46, wherein the lower alcohol is selected from ethanol and isopropanol.

48. The process according to claim 47, wherein the lower alcohol is isopropanol.

49. The process according to claim 41, wherein the lower alcohol is used at the amount of 2~4 times of the weight of the wet grains of gellan gum.

50. The process according to claim 49, wherein the lower alcohol is used at the amount of 2.5~3.5 times of the weight of the wet grains of gellan gum.

51. The process according to claim 1, wherein, in Step (7), the drying and milling is to dry the product obtained in Step (6) at a temperature of 75~80° C., and mill the dried product and granulate it into granules.

52. The process according to claim 51, wherein the drying device is selected from a vacuum dryer and a boiling dryer, and the drying time is in the range of 1 to 1.5 hours.

* * * * *